United States Patent
Dassler et al.

(10) Patent No.: US 9,347,078 B2
(45) Date of Patent: May 24, 2016

(54) METHOD FOR THE FERMENTATIVE PRODUCTION OF L-CYSTEINE AND DERIVATIVES OF SAID AMINO ACID

(71) Applicant: Wacker Chemie AG, Munich (DE)

(72) Inventors: Tobias Dassler, Munich (DE); Walfred Leinfelder, Kastl (DE); Guenter Wich, Munich (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 14/427,238

(22) PCT Filed: Sep. 9, 2013

(86) PCT No.: PCT/EP2013/068629
§ 371 (c)(1),
(2) Date: Mar. 10, 2015

(87) PCT Pub. No.: WO2014/040955
PCT Pub. Date: Mar. 20, 2014

(65) Prior Publication Data
US 2015/0232897 A1 Aug. 20, 2015

(30) Foreign Application Priority Data
Sep. 17, 2012 (DE) .................. 10 2012 216 527

(51) Int. Cl.
C12P 13/12 (2006.01)
C12P 17/14 (2006.01)

(52) U.S. Cl.
CPC *C12P 13/12* (2013.01); *C12P 17/14* (2013.01)

(58) Field of Classification Search
None
See application file for complete search history.

(56) References Cited

U.S. PATENT DOCUMENTS

| | | | |
|---|---|---|---|
| 5,972,663 A | 10/1999 | Winterhalter et al. | |
| 6,218,168 B1 | 4/2001 | Leinfelder et al. | |
| 6,620,598 B2 | 9/2003 | Maier et al. | |
| 8,802,399 B2 * | 8/2014 | Reutter-Maier ........ | C12P 13/12 435/113 |
| 9,074,230 B2 * | 7/2015 | Dassler ................... | C12P 13/12 |
| 2004/0038352 A1 | 2/2004 | Maier | |
| 2005/0009162 A1 | 1/2005 | Maier et al. | |
| 2005/0221453 A1 | 10/2005 | Takagi et al. | |
| 2009/0053778 A1 | 2/2009 | Sauer et al. | |
| 2009/0226984 A1 | 9/2009 | Nonaka et al. | |
| 2014/0080186 A1 | 3/2014 | Dassler et al. | |

FOREIGN PATENT DOCUMENTS

| | | |
|---|---|---|
| CA | 2386539 A1 | 4/2002 |
| DE | 102011075656 A1 | 3/2012 |
| EP | 0235908 A2 | 9/1987 |
| EP | 0620853 B1 | 3/1996 |
| EP | 0885962 A1 | 12/1998 |
| EP | 1233067 B1 | 5/2004 |
| EP | 1382684 B1 | 12/2005 |
| EP | 1571223 B1 | 1/2010 |
| EP | 2138585 B1 | 2/2011 |
| WO | 2004113373 A1 | 12/2004 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
N. M. Kredich, editors: F. C. Neidhardt, R. Curtiss III, J. L. Ingraham, E. C. C. Lin, K. B. Low, B. Magasanik, W. S. Reznikoff, M. Riley, M. Schaechter, and H. E. Umbarger, "Biosynthesis of Cysteine", *Escherichia coli* and *Salmonella*: cellular and molecular biology, 1996, pp. 514-527, 2nd edition, ASM Press, Washington, D.C.
H. Hama et al., Inhibition of Homoserine Dehydrogenase I by L-Serine in *Escherichia coli*, J. Biochem., 1991, pp. 604-608, vol. 109.
P. Datta, Regulation of Homoserine Biosynthesis by L-Cysteine, a Terminal Metabolite of a Linked Pathway, Biochemistry, 1967, pp. 635-641, vol. 58.
Ch. L. Harris, Cysteine and Growth Inhibition of *Escherichia coli*: Threonine Deaminase as the Target Enzyme, Journal of Bacteriology, 1981, pp. 1031-1035, vol. 145, No. 2.
I. Raskó et al., Biosynthetic L-Threonine Deaminase as the Origin of L-Serine Sensitivity of *Escherichia coli*, Eur. J. Biochem, 1971, pp. 424-427, vol. 21.
T. Dassler et al., Identification of a Major Facilitator Protein from *Escherichia coli* Involved in Efflux of Metabolites of the Cysteine Pathway, Molecular Microbiology 2000, pp. 1101-1112, vol. 36, No. 5, Blackwell Science Ltd.
S. Nakamori et al., Overproduction of L-Cysteine ud L-Cystine by *Escherichia coli* Strains with a Genetically Altered Serine Acetyltransferase, Applied and Environmental Microbiology, 1998, pp. 1607-1611, vol. 64, No. 5, American Society for Microbiology.
M. K. Gaitonde, A Spectrophotometric Method for the Direct Determination of Cysteine in the Presence of Other Naturally Occurring Amino Acids, Biochem. J., 1967, pp. 627-633, vol. 104.
English Abstract for definition of the term "Wildtyp" (wild type) from www.biologie-lexikon.de (2015).
English Abstract for H. Ibelgaufts, Gentechnologie von A bis Z (Genetic Engineering from A to Z), Definition of the term "Wildtyp" (wild type), p. 474, Wiley-VCH (1993).
International Search Report for PCT/EP2013/068629 dated Oct. 25, 2013.

* cited by examiner

*Primary Examiner* — Christian Fronda
(74) *Attorney, Agent, or Firm* — Caesar Rivise, PC

(57) ABSTRACT

The invention relates to a method for producing L-cysteine and its derivatives L-cystine and thiazolidine by fermenting a cysteine-producing microorganism strain in a fermentation medium. The invention is characterized in that L-methionine, L-isoleucine, or L-threonine in respective concentrations ranging from 0.1 to 10 g/L are added to the fermentation medium in the main culture.

13 Claims, No Drawings

METHOD FOR THE FERMENTATIVE PRODUCTION OF L-CYSTEINE AND DERIVATIVES OF SAID AMINO ACID

BACKGROUND OF THE INVENTION

The invention relates to a method for the fermentative production of L-cysteine and derivatives of said amino acid L-cystine and 2-methylthiazolidine-2,4-dicarboxylic acid.

L-Cystine is a disulfide that is formed on the oxidation of two molecules of L-cysteine. This reaction is reversible, which means that L-cystine can be converted by reduction back into L-cysteine.

2-Methylthiazolidine-2,4-dicarboxylic acid (thiazolidine) is the condensation product of L-cysteine and pyruvate, which is formed in a purely chemical reaction (U.S. Pat. No. 5,972,663A). This reaction is likewise reversible. Thus, the thiazolidine can be decomposed, e.g. in acids at elevated temperature, back to its starting components.

The amino acid L-cysteine is of economic importance. It is used, for example, as food additive (in particular in the baking agent industry), as feedstock in cosmetics, and also as raw material for the production of pharmaceutical active ingredients (in particular N-acetylcysteine and S-carboxymethylcysteine).

L-Cysteine, in all organisms, takes a key position in sulfur metabolism and is used in the synthesis of proteins, glutathione, biotin, lipoic acid, methionine and other sulfur-containing metabolites. In addition, L-cysteine serves as a precursor for the biosynthesis of coenzyme A. The biosynthesis of L-cysteine has been studied in bacteria, in particular in enterobacteria, in detail and is extensively described in Kredich (1996, Biosynthesis of cysteine, p. 514-527. In F. C. Neidhardt, R. Curtiss III, J. L. Ingraham, E. C. C. Lin, K. B. Low, B. Magasanik, W. S. Reznikoff, M. Riley, M. Schaechter, and H. E. Umbarger (ed.), *Escherichia coli* and *Salmonella*: cellular and molecular biology, 2nd ed. ASM Press, Washington, D.C.).

An important precursor from central metabolism in L-cysteine biosynthesis is 3-phosphoglycerate, an intermediate of glycolysis. L-Cysteine is therefore, together with L-serine and glycine, considered as part of the phosphoglycerate family. The proteinogenic amino acids L-methionine, L-isoleucine and L-threonine, in contrast, belong to the oxaloacetate family, since the shared precursor from central metabolism is the citric acid cycle intermediate oxaloacetate. Proceeding from a carbon source such as, for example, glucose, the material flow proceeds via these two different branches of the assimilatory amino acid metabolism very largely independently of one another. However, certain interactions of intermediates or end products of the phosphoglycerate family with individual biosynthesis steps of the oxaloacetate family are known. For instance, it has been described that homoserine dehydrogenase I, the thrA gene product which catalyzes the reduction of L-aspartate semialdehyde to L-homoserine, can be inhibited not only by L-serine, but also by L-cysteine (Hama et al., 1991, J. Biochem. 109, 604-8; Datta, 1967, Biochemistry 58, 635-41). Furthermore, it is known that the assimilatory threonine deaminase IlvA is inhibited by L-cysteine (Harris, 1981, J. Bacteriol. 145, 1031-35). In addition, L-serine—analogously to L-threonine—can serve as a substrate of the IlvA gene product (Rasko et al., 1971, Eur. J. Biochem. 21, 424-27).

Although it is described in various patents that L-isoleucine can be added to the culture medium in the fermentative production of amino acids of the phosphoglycerate family (EP1233067, EP1382684), L-isoleucine is cited therein only as one of various possible additions. The fact that L-isoleucine could possibly have a beneficial effect on the amino acid production, however, is not indicated or rendered obvious at any point.

In Dassler et al. (2000, Mol. Microbiol. 36: 1101-1112), the addition of the amino acids L-methionine, L-isoleucine and L-leucine to the medium of the preculture (in each case 0.3 g/l) in the fermentative production of amino acids of the phosphoglycerate family is described. However, these amino acids were not added to the medium of the main culture in the fermenter. Here also, there is no indication that the amino acid supplementation of the preculture medium could have a beneficial effect on the production of cysteine or acetylserine.

In addition to the classical production of L-cysteine by means of extraction from keratinaceous material such as hairs, bristles, horns, hooves and feathers, or by means of biotransformation by enzymatic conversion of precursors, some years ago, a method was also developed for the fermentative production of L-cysteine. The prior art with respect to the fermentative production of L-cysteine by microorganisms is described, e.g., in U.S. Pat. Nos. 6,218,168B1, 5,972,663A, US20040038352A1, CA2386539A1, US20090053778A1 and US20090226984A1. Bacterial host organisms used here are, inter alia, strains of the genera *Corynebacterium* and also representatives of the Enterobacteriaceae family such as, e.g., *Escherichia coli* or *Pantoea ananatis*.

In addition to the classical procedure to arrive at improved L-cysteine producers by mutation and selection, genetic modifications to the strains were also performed in a targeted manner in order to achieve effective L-cysteine overproduction.

Thus, the introduction of a cysE allele, which encodes a serine-O-acetyl transferase having reduced feedback inhibition by L-cysteine, led to an increase in cysteine production (U.S. Pat. No. 6,218,168B1; Nakamori et al., 1998, Appl. Env. Microbiol. 64: 1607-1611). The formation of O-acetyl-L-serine, the direct precursor of L-cysteine, is substantially decoupled from the L-cysteine level of the cell by a feedback-resistant CysE enzyme.

O-Acetyl-L-serine is formed from L-serine and acetyl-CoA. Therefore, providing L-serine in a sufficient amount for L-cysteine production is of great importance. This can be achieved by introducing a serA allele which encodes a 3-phosphoglycerate dehydrogenase having reduced feedback inhibition by L-serine. As a result, the formation of 3-hydroxypyruvate, a precursor of L-serine, is substantially decoupled from the L-serine level of the cell. Examples of such SerA enzymes are described in EP0620853 and US2005009162A2.

In addition, it is known that the L-cysteine yield in the fermentation can be increased by attenuating or destroying genes which encode L-cysteine-degrading enzymes, such as, e.g., the tryptophanase TnaA or the cystathionine-β-lyases MalY or MetC (EP1571223).

Increasing the transport of L-cysteine out of the cell is a further possibility for increasing the product yield in the medium. This can be achieved by overexpression of what are termed efflux genes. These genes encode membrane-bound proteins which mediate the export of L-cysteine out of the cell. Various efflux genes have been described for L-cysteine export (U.S. Pat. No. 5,972,663A, US20040038352A1).

The export of L-cysteine out of the cell into the fermentation medium has many advantages:

1) L-Cysteine is continuously withdrawn from the intracellular reaction equilibrium with the consequence that the level of this amino acid in the cell is kept low, and therefore there is no feedback inhibition of sensitive enzymes due to L-cysteine:
(1) L-cysteine (intracellular)⇌L-cysteine (medium)
2) The L-cysteine secreted into the medium is oxidized to the disulfide L-cystine in the presence of oxygen which is introduced into the medium during the culturing (U.S. Pat. No. 5,972,663A):
  (2) 2 L-cysteine+½$O_2$⇌L-cystine+$H_2O$ Since the solubility of L-cystine in aqueous solution at a neutral pH is only very low, especially in comparison to L-cysteine, the disulfide precipitates out even at a low concentration, and forms a white precipitate:
  (3) L-cystine (dissolved)⇌L-cystine (precipitate) Owing to the precipitation of L-cystine, the level of the product dissolved in the medium is lowered, as a result of which also in each case the reaction equilibrium of (1) and (2) is shifted to the product side.
3) The technical expenditure for purifying the product is markedly lower when the amino acid can be obtained directly from the fermentation medium, than when the product accumulates intracellularly and a cell digestion must proceed first.

The expression "total cysteine", in the context of this invention, combines L-cystine and the compounds L-cystine and thiazolidine formed therefrom, which are formed during fermentation and accumulate in the culture supernatant and in the precipitate.

In addition to genetic modification of the L-cysteine production strain, optimizing the fermentation method, i.e. the type and manner of culturing the cells, also plays an important role in the development of an efficient production process.

In this case, various culture parameters such as, e.g., the type and dosage of the carbon and energy sources, the temperature, the supply with oxygen (DE102011075656A1), the pH, and also the composition of the culture medium, can affect the product yield and/or the product spectrum in the fermentative production of L-cysteine.

On account of the continually increasing raw material and energy costs, there is constantly the need to increase the product yield in the production of L-cysteine, in order, in this manner, to improve the economic efficiency of the process.

DESCRIPTION OF THE INVENTION

It is the object of the present invention to provide an improved method for the production of L-cysteine and its derivatives L-cystine and thiazolidine by means of fermentation of a cysteine-producing microorganism strain in a fermentation medium in a preculture and a main culture in a fermenter.

The object is achieved by a method which is characterized in that L-methionine, L-isoleucine or L-threonine are added to the fermentation medium in the main culture each in a concentration range from 0.1 to 10 g/l.

In a screening of various chemical substances with respect to their effect on the production process, it was surprisingly found that by supplementing the fermentation medium in the main culture with the amino acids L-methionine, L-isoleucine or L-threonine, the total cysteine yield can be increased. This is all the more astonishing since the bacterial strains which customarily are used for a process for the fermentative cysteine production are prototrophic with respect to said amino acids.

A beneficial effect of supplementing L-methionine, L-isoleucine or L-threonine on the fermentative production of L-cysteine and the abovementioned derivatives of this amino acid in the main culture has not been described or rendered obvious to date. The fact that the yield in a fermentative cysteine production process can be increased by adding these amino acids is surprising principally because none of these amino acids is a metabolic precursor in cysteine biosynthesis.

L-Methionine, L-isoleucine or L-threonine are added to the fermentation medium in the main culture each in a concentration range of preferably 0.5-5 g/l, particularly preferably 0.5-3 g/l each.

In this case, the combinations methionine/isoleucine and methionine/threonine are preferred over supplementation with only one single amino acid. Particular preference in this case is given to the combination methionine/isoleucine. When an amino acid combination is added, the same concentration ranges are preferred as are cited for the individual amino acids.

Supplementing the medium with the corresponding amino acids can proceed as a batch addition even at the start of culturing the main culture. Alternatively, the amino acids can be added to the medium continuously first during the fermentation.

Cysteine production in the main culture (production culture) proceeds in principle according to a fermentation method known to those skilled in the art in a bioreactor, preferably a stirred-tank fermenter, having a volume of at least 5 $m^3$, preferably at least 20 $m^3$, particularly preferably at least 50 $m^3$. Culturing the cysteine-producing cells is typically carried out in a plurality of stages. Proceeding from a stock culture, the cells are initially grown in at least one preculture, before finally the main culture is inoculated with the last preculture. In this case, generally a successive scale-up proceeds from shake flask via fermenters on a laboratory scale up to the bioreactor on an industrial scale.

As microorganisms for the method according to the invention, all cysteine-producing strains described in the prior art can be used. Such strains are, for example, disclosed in U.S. Pat. Nos. 6,218,168B1, 5,972,663A, US20040038352A1, CA2386539A1, US20090053778 or EP2138585.

As microorganism strains, preference is given to representatives of the Enterobacteriaceae family, particular preference to representatives of the genera *Escherichia* and *Pantoea*, very particular preference is given to strains of the species *E. coli* and *P. ananatis*.

Of these microorganism strains, again strains are preferred which either possess a modified serine-O-acetyl transferase which, in comparison with the corresponding wild type enzyme, has a feedback inhibition due to L-cysteine decreased by least the factor 2, or which have a cysteine export out of the cell increased by at least the factor 2 in comparison with a wild type cell by overexpression of an efflux gene. Particularly preferred microorganism strains not only possess a serine-O-acetyl transferase which, in comparison with the corresponding wild type enzyme, has a feedback inhibition due to L-cysteine decreased by at least the factor 2, but also has a cysteine export out of the cell increased by at least the factor 2 in comparison with a wild type cell by overexpression of an efflux gene. Such strains are known, for example, from U.S. Pat. Nos. 6,218,168B1 and 5,972,663A. Very particularly preferred strains are those which in addition, possess a modified 3-phosphoglycerate dehydrogenase having a feedback inhibition due to L-serine decreased by at least the factor 2 in comparison with the corresponding wild type enzyme (US2005009162A2) and in which at least one L-cysteine-degrading enzyme is attenuated so far that, in the cell, only a maximum of 50% of this enzyme activity is present in comparison with a wild type cell.

Preferred variants of the serine-O-acetyl transferase have a feedback inhibition due to L-cysteine that is reduced in comparison with the corresponding wild type enzyme by at least the factor 5, particularly preferably by at least the factor 10, very particularly preferably by at least the factor 50.

The efflux gene originates preferably from the group ydeD (see U.S. Pat. No. 5,972,663A), yfiK (see US20040038352A1), cydDC (see WO2004113373), bcr (see US2005221453) and emrAB (see US2005221453) of *E. coli* or the corresponding homologous gene from another microorganism. A homologous gene is taken to mean that the sequence of said gene is at least 80% in agreement with the DNA sequence of the corresponding *E. coli* gene.

The overexpression of an efflux gene leads to cysteine export out of the cell being increased in comparison with a wild type cell preferably by at least the factor 5, particularly preferably by at least the factor 10, very particularly preferably by at least the factor 20.

Preferred variants of the 3-phosphoglycerate dehydrogenase have a feedback inhibition due to L-serine that is decreased in comparison with the corresponding wile type enzyme by at least the factor 5, particularly preferably by at least the factor 10, very particularly preferably by at least the factor 50.

The L-cysteine-degrading enzyme preferably originates from the group tryptophanase (TnaA) and cystathionine-β-lyase (MalY, MetC).

Particular preference is given to microorganism strains in which at least one of these enzymes is attenuated to the point that only a maximum of 10% of the enzyme activity is still present in the cell, in comparison with a wild type strain. Very particular preference is given to strains in which at least one of these enzymes is completely inactivated.

The cells are cultured in the case of L-cysteine production under aerobic growth conditions, wherein the oxygen content during the fermentation in the main culture is set at a maximum 50% saturation. The oxygen saturation in the culture is in this case regulated automatically via the gas feed and the stirring speed.

As carbon source, preferably sugars, sugar alcohols, organic acids or sugar-containing plant hydrolysates are used. Particularly preferably, as carbon source, glucose, fructose, lactose, glycerol or mixtures which comprise two or more of these compounds are used in the method according to the invention.

The production phase of the fermentation method according to the invention starts with the time point at which L-cysteine, L-cystine or thiazolidine can be detected for the first time in the culture broth of the main culture and lasts until the end of culturing. Typically, this phase starts approximately 8-10 h after inoculation of the production fermenter.

Preferably, the carbon source is added to the main culture in such a manner that the content of the carbon source in the fermenter does not exceed 10 g/l during the production phase. Preference is given to a maximum concentration of 2 g/l, particular preference of 0.5 g/l, very particular preference of 0.1 g/l.

As N source in the method according to the invention, preferably ammonia, ammonium salts or protein hydrolysates are used. When ammonia is used as correction medium for pH-stating, this N source is regularly supplemented during the fermentation.

As further media additives, salts of the elements phosphorus, chlorine, sodium, magnesium, nitrogen, potassium, calcium, iron, and, in traces (i.e. in μM concentrations) salts of the elements molybdenum, boron, cobalt, manganese, zinc and nickel can be added.

In addition, organic acids (e.g. acetate, citrate) and vitamins (e.g. B1, B6) can be added to the medium.

As complex nutrient sources, e.g. yeast extract, corn steep liquor, soybean flour or malt extract can be used.

The incubation temperature for mesophilic microorganisms such as, e.g., *E. coli* or *P. ananatis* is preferably 15-45° C., particularly preferably 30-37° C.

The pH of the fermentation medium is preferably in the pH range from 5.5 to 7.5 during the fermentation, particular preference is given to a pH of 6.5-7.5, very particular preference to a pH of 7.0.

For the production of L-cysteine and L-cysteine derivatives, during the fermentation a sulfur source must be supplied. Preferably, sulfates or thiosulfates are used here.

Microorganisms which are fermented according to the method described secrete L-cysteine and compounds derived therefrom into the fermentation medium in high efficiency in a batch process or fed batch process, after an initial growth phase, in a period of from 8 to 150 hours.

After the fermentation, the L-cystine present as precipitate can be separated off using known methods from the residual components of the culture broth, for example using a decanter.

For further purification of the crude product, the following steps can be carried out:
Dissolving the crude product with a mineral acid
Clarifying the crude product solution by centrifugation or filtration
Decolorizing the solution
Precipitation crystallization.

The reduction of L-cystine to L-cysteine can proceed, for example, via an electrochemical process, as described in EP0235908.

The examples hereinafter serve to further illustrate the invention.

EXAMPLE 1

Generation of Cysteine Production Strains

The wild type strains *E. coli* W3110 (ATCC 27325) and *P. ananatis* (ATCC 11530) were each transformed using the plasmid pACYC184/cysEX-GAPDH-ORF306 (disclosed in example 2 of U.S. Pat. No. 5,972,663A) by electroporation as described in U.S. Pat. No. 5,972,663A. The plasmid pACYC184/cysEX-GAPDH-ORF306, in addition to the replication origin and a tetracycline resistance gene, also further contains the cysEX allele which encodes a serine-O-acetyl transferase having a reduced feedback inhibition due to L-cysteine, and also the efflux gene ydeD (ORF306), the expression of which is controlled by the constitutive GAPDH promoter.

Plasmid-bearing cells were selected on LB agar plates which contained 15 mg/l tetracycline.

After a repeated plasmid isolation by means of the QIAprep Spin Plasmid Kit (Qiagen GmbH) and a restriction analysis, the desired transformants, i.e. cells which have taken up the plasmid pACYC184/cysEX-GAPDH-ORF306 were isolated and used in the culturing which is described in examples 2 and 3.

EXAMPLE 2

Cysteine Production with Supplementation of Various Amino Acids

Preculture 1:
20 ml of LB medium containing 15 mg/l of tetracycline were inoculated in an Erlenmeyer flask (100 ml) with the respective strain (*E. coli* W3110 pACYC184/cysEX-GAPDH-ORF306 or *P. ananatis* pACYC184/cysEX-GAPDH-ORF306) and incubated for seven hours on a shaker (150 rpm, 30° C.).

Preculture 2:

Then, preculture 1 was completely transferred to 100 ml of SM1 medium (12 g/l $K_2HPO_4$, 3 g/l $KH_2PO_4$, 5 g/l $(NH_4)_2SO_4$, 0.3 g/l $MgSO_4.7H_2O$, 0.015 g/l $CaCl_2.2H_2O$, 0.002 g/l $FeSO_4.7H_2O$, 1 g/l $Na_3$ citrate.2H2O, 0.1 g/l NaCl, 1 ml/l of trace element solution consisting of 0.15 g/l $Na_2MoO_4.2H_2O$, 2.5 g/l $H_3BO_3$, 0.7 g/l $CoCl_2.6\ H_2O$, 0.25 g/l $CuSO_4.5\ H_2O$, 1.6 g/l $MnCl_2.4H_2O$, 0.3 g/l $ZnSO_4.7\ H_2O$), which was supplemented with 5 g/l of glucose, 5 mg/l of vitamin B1 and 15 mg/l of tetracycline. The cultures were shaken in Erlenmeyer flasks (1 l) at 30° C. for 17 h at 150 rpm. After this incubation, the optical density at 600 nm ($OD_{600}$) was between 3 and 5.

Main Culture:

The fermentation was carried out in fermenters of the BIOSTAT B type from Sartorius Stedim. A culture vessel having a total volume 2 l was used. The fermentation medium (900 ml) contains 15 g/l of glucose, 10 g/l of tryptone (Difco), 5 g/l of yeast extract (Difco), 5 g/l $(NH_4)_2SO_4$, 1.5 g/l $KH_2PO_4$, 0.5 g/l NaCl, 0.3 g/l $MgSO_4.7\ H_2O$, 0.015 g/l $CaCl_2.2\ H_2O_4$, 0.075 g/l $FeSO_4.7H_2O$, 1 g/l $Na_3$ citrate.2 $H_2O$ and 1 ml of trace element solution (see above), 0.005 g/l of vitamin B1 and 15 mg/l of tetracycline. In various experimental setups, in addition the amino acids L-methionine, L-isoleucine or L-threonine were also added to the medium, either individually or in combination in various concentrations (see Table 1).

The pH in the fermenter was set at the start to 7.0 by pumping in a 25% $NH_4OH$ solution. During the fermentation, the pH was kept at 7.0 by automatic correction using 25% $NH_4OH$. For inoculation, 100 ml of the preculture 2 were pumped into the fermenter vessel. The initial volume was therefore about 1 l. The cultures were stirred at the start at 400 rpm and aerated with 2 vvm of compressed air that was sterilized via a sterile filter. Under these initial conditions, the oxygen probe had been calibrated to 100% saturation before inoculation. The target value for the $O_2$ saturation during fermentation was set to 50%. After the $O_2$ saturation had fallen below the target value, a regulation cascade was started in order to lead the $O_2$ saturation back to the target value. In this case, first the gas feed was continuously increased (to a max. 5 vvm) and then the stirrer speed was continuously increased (to a max. 1500 rpm). The fermentation was carried out at a temperature of 30° C. After a fermentation time of 2 h, a sulfur source in the form of a sterile 60% sodium thiosulfate.5 $H_2O$ stock solution was supplied at a rate of 1.5 ml per hour. As soon as the glucose content in the fermenter had fallen from initially 15 g/l to approximately 2 g/l, a 56% glucose solution was added continuously. The feed rate was set in such a manner that the glucose concentration in the fermenter then no longer exceeded 2 g/l. The glucose was determined using a glucose analyzer from YSI (Yellow Springs, Ohio, USA).

The fermentation period was 48 hours. Thereafter, samples were withdrawn and the content of L-cysteine and the derivatives derived therefrom were determined in each case separately from one another in the culture supernatant (primarily L-cysteine and thiazolidine) and in the precipitate (L-cystine) (see Table 1). For this purpose, in each case the colorimetric test of Gaitonde was used (Gaitonde, M. K. (1967), Biochem. J. 104, 627-633). Here, it is necessary to take into account the fact that the test, under the strongly acidic reaction conditions, does not discriminate between L-cysteine and the condensation product of L-cysteine and pyruvate, 2-methyl-thiazolidine-2,4-dicarboxylic acid (thiazolidine) which is described in EP0885962 A1. L-Cystine, which is formed by oxidation of two L-cysteine molecules, likewise detected as L-cysteine in the test by reduction with dithiothreitol in dilute solution at pH 8.0. The L-cystine situated in the precipitate first had to be dissolved in 8% hydrochloric acid before it was able to be quantified in the same manner.

TABLE 1

Content of L-cysteine and L-cysteine derivatives in the culture broth after 48 h

| Amino acid addition [g/l] | Cysteine content [g/l] after 48 h | | | | | |
|---|---|---|---|---|---|---|
| | E. coli | | | P. ananatis | | |
| | Supernatant[1] | Precipitate[2] | Total cysteine[3] | Supernatant[1] | Precipitate[2] | Total cysteine[3] |
| — | 6.1 | 10.8 | 16.9 | 3.4 | 7.6 | 11.0 |
| Met 1.5 | 6.2 | 11.3 | 17.5 | 3.5 | 8.4 | 11.9 |
| Ile 1.5 | 6.5 | 11.3 | 17.8 | 3.7 | 8.0 | 11.7 |
| Thr 1.5 | 6.3 | 11.0 | 17.3 | 3.5 | 8.3 | 11.8 |
| Met/Ile 0.1/0.1 | 6.8 | 13.1 | 19.9 | 4.0 | 9.2 | 13.2 |
| Met/Ile 0.5/0.5 | 7.1 | 14.4 | 21.5 | 4.2 | 10.5 | 14.7 |
| Met/Ile 3/3 | 7.3 | 16.3 | 23.6 | 4.1 | 11.2 | 15.3 |
| Met/Ile 10/10 | 7.5 | 16.0 | 23.5 | 4.3 | 11.0 | 15.3 |
| Met/Thr 0.1/0.1 | 6.8 | 12.2 | 19.0 | 3.9 | 9.0 | 12.9 |
| Met/Thr 0.5/0.5 | 7.2 | 13.6 | 20.8 | 4.2 | 9.8 | 14.0 |
| Met/Thr 3/3 | 7.2 | 14.9 | 22.1 | 4.0 | 11.0 | 15.0 |
| Met/Thr 10/10 | 7.4 | 14.6 | 22.0 | 4.6 | 10.3 | 14.9 |

[1]Sum of the L-cysteine, L-cystine and thiazolidine dissolved in the supernatant
[2]L-Cystine in the precipitate
[3]Total cysteine (sum of supernatant and precipitate)

The invention claimed is:

1. A method for producing L-cysteine and its derivatives L-cystine and thiazolidine, said method comprising fermentation of a cysteine-producing microorganism strain in a fermentation medium in a preculture and a main culture in a fermenter, wherein L-methionine, L-isoleucine or L-threonine is added to the fermentation medium in the main culture each in a concentration range from 0.5 to 5 g/l.

2. The method as claimed in claim 1, wherein methionine and isoleucine or methionine and threonine are added.

3. The method as claimed in claim 2, wherein methionine and isoleucine are added.

4. The method as claimed in claim 1, wherein the cysteine-producing microorganism strain is a representative of the *Enterobacteriaceae* family.

5. The method as claimed in claim 1, wherein the cysteine-producing microorganism strain either possesses a modified serine-O-acetyl transferase which, in comparison with a corresponding wild type enzyme, has a feedback inhibition due to L-cysteine decreased by least a factor of 2, or which has a cysteine export out of a cell increased by at least a factor of 2 in comparison with a wild type cell by overexpression of an efflux gene.

6. The method as claimed in claim 1, wherein the cysteine-producing microorganism strain not only has a serine-O-acetyl transferase which, in comparison with a corresponding wild type enzyme, has a feedback inhibition due to L-cysteine decreased by at least a factor of 2, but also has a cysteine export out of a cell increased by at least a factor of 2 in comparison with a wild type cell by overexpression of an efflux gene, and also, in addition, a modified 3-phosphoglycerate dehydrogenase having a feedback inhibition due to L-serine decreased by at least a factor of 2 in comparison with the corresponding wild type enzyme and in which at least one L-cysteine-degrading enzyme is attenuated so far that, in the cell, only a maximum of 50% of L-crysteine-degrading enzyme activity is present in comparison with a wild type cell.

7. The method as claimed in claimed 1, wherein cells are cultured in the case of L-cysteine production under aerobic growth conditions, wherein an oxygen content during the fermentation is set at a maximum 50% saturation.

8. The method as claimed in claim 1, wherein a carbon source is added in such a manner that a content of the carbon source in the fermentation medium does not exceed 10 g/l during a production phase.

9. The method as claimed in claim 3, wherein the cysteine-producing microorganism strain is a representative of the *Enterobacteriaceae* family.

10. The method as claimed in claim 9, wherein the cysteine-producing microorganism strain either possesses a modified serine-O-acetyl transferase which, in comparison with a corresponding wild type enzyme, has a feedback inhibition due to L-cysteine decreased by least a factor of 2, or which has a cysteine export out of a cell increased by at least a factor of 2 in comparison with a wild type cell by overexpression of an efflux gene.

11. The method as claimed in claim 10, wherein the cysteine-producing microorganism strain not only has a serine-O-acetyl transferase which, in comparison with a corresponding wild type enzyme, has a feedback inhibition due to L-cysteine decreased by at least a factor of 2, but also has a cysteine export out of a cell increased by at least a factor of 2 in comparison with a wild type cell by overexpression of an efflux gene, and also, in addition, a modified 3-phosphoglycerate dehydrogenase having a feedback inhibition due to L-serine decreased by at least a factor of 2 in comparison with the corresponding wild type enzyme and in which at least one L-cysteine-degrading enzyme is attenuated so far that, in the cell, only a maximum of 50% of L-cysteine-degrading enzyme activity is present in comparison with a wild type cell.

12. The method as claimed in claim 11, wherein cells are cultured in the case of L-cysteine production under aerobic growth conditions, wherein an oxygen content during the fermentation is set at a maximum 50% saturation.

13. The method as claimed in claim 12, wherein a carbon source is added in such a manner that a content of the carbon source in the fermentation medium does not exceed 10 g/l during a production phase.

* * * * *